(12) United States Patent
Rousseau et al.

(10) Patent No.: US 7,828,854 B2
(45) Date of Patent: Nov. 9, 2010

(54) IMPLANTABLE REPAIR DEVICE

(75) Inventors: Robert A. Rousseau, Ottsville, PA (US); David C. Lindh, Sr., Flemington, NJ (US); John R. Jacobs, Easton, PA (US); Ilya S. Koyfman, Ringoes, NJ (US); Gaoyuan Gavin Chen, Hillsborough, NJ (US); Donald G. Hill, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 615 days.

(21) Appl. No.: 11/554,909

(22) Filed: Oct. 31, 2006

(65) Prior Publication Data

US 2008/0147200 A1  Jun. 19, 2008

(51) Int. Cl.
*A61F 2/02* (2006.01)

(52) U.S. Cl. .................................. 623/23.72; 606/151

(58) Field of Classification Search ................ 606/151; 623/23.72
See application file for complete search history.

(56) References Cited

U.S. PATENT DOCUMENTS

| | | | |
|---|---|---|---|
| 5,116,357 A | 5/1992 | Eberbach | |
| 5,147,374 A | 9/1992 | Fernandez | |
| 5,356,432 A | 10/1994 | Rutkow et al. | |
| 5,456,720 A | 10/1995 | Schultz et al. | |
| 5,733,294 A * | 3/1998 | Forber et al. | 606/151 |
| 5,972,008 A | 10/1999 | Kalinski et al. | |
| 6,030,337 A * | 2/2000 | Grant et al. | 600/29 |
| 6,113,623 A | 9/2000 | Sgro | |
| 6,224,616 B1 | 5/2001 | Kugel | |
| 6,274,786 B1 | 8/2001 | Heller | |
| 6,306,079 B1 * | 10/2001 | Trabucco | 600/30 |
| 6,383,201 B1 | 5/2002 | Dong | |
| 6,436,030 B2 | 8/2002 | Rehil | |
| 6,447,524 B1 | 9/2002 | Knodel et al. | |
| 6,596,002 B2 | 7/2003 | Therin et al. | |
| 6,599,318 B1 | 7/2003 | Gabbay | |
| 6,623,492 B1 | 9/2003 | Berube et al. | |
| 6,669,735 B1 | 12/2003 | Pelissier | |
| 6,736,854 B2 * | 5/2004 | Vadurro et al. | 623/23.72 |
| 6,991,637 B2 | 1/2006 | Crawley et al. | |
| 7,101,381 B2 | 9/2006 | Ford et al. | |

(Continued)

FOREIGN PATENT DOCUMENTS

EP  0130037 A1  1/1985

(Continued)

*Primary Examiner*—(Jackie) Tan-Uyen T Ho
*Assistant Examiner*—Alexander Orkin
(74) *Attorney, Agent, or Firm*—Emil Richard Skula

(57) ABSTRACT

An implantable prosthesis for repairing or reinforcing a tissue or muscle wall defect including a first composite structure including at least one layer of a non-absorbable material is disclosed. The first composite structure has a central portion sized and shaped to cover at least a portion of the tissue or muscle wall defect, and has an outer periphery. The prosthesis further includes a second structure having a reinforced central region and an outer peripheral edge, a reinforcing element positioned between the first and second structures, and having an outer periphery and a stiffness greater than that of the first and second structures, and at least one pulling element coupled to the reinforced central region of the second structure. The second structure is coupled to the first structure substantially only at their respective peripheries.

19 Claims, 7 Drawing Sheets

U.S. PATENT DOCUMENTS

| | | |
|---|---|---|
| 2001/0044637 A1 | 11/2001 | Jacobs et al. |
| 2001/0049539 A1 | 12/2001 | Rehil |
| 2002/0049503 A1 | 4/2002 | Milbocker |
| 2002/0103494 A1 | 8/2002 | Pacey |
| 2004/0039453 A1* | 2/2004 | Anderson et al. ........ 623/23.72 |
| 2004/0049207 A1 | 3/2004 | Goldfarb et al. |
| 2004/0087980 A1 | 5/2004 | Ford et al. |
| 2004/0087981 A1 | 5/2004 | Berube et al. |
| 2004/0092969 A1 | 5/2004 | Kumar |
| 2004/0204723 A1 | 10/2004 | Kayan |
| 2005/0010239 A1 | 1/2005 | Chefitz |
| 2005/0113858 A1 | 5/2005 | Deutsch |
| 2005/0192600 A1 | 9/2005 | Nicolo et al. |
| 2005/0267325 A1* | 12/2005 | Bouchier et al. ............... 600/37 |

FOREIGN PATENT DOCUMENTS

| | | | |
|---|---|---|---|
| EP | 0130037 | B1 | 11/1987 |
| EP | 0898944 | A2 | 3/1998 |
| EP | 1199037 | A2 | 4/2002 |
| EP | 1219265 | A2 | 7/2002 |
| EP | 0898944 | B1 | 5/2004 |
| WO | WO 9529635 | A1 | 11/1995 |
| WO | WO 9956664 | A1 | 11/1999 |
| WO | WO 0189392 | A2 | 11/2001 |
| WO | WO 0222047 | A1 | 3/2002 |
| WO | WO 03034925 | A2 | 5/2003 |
| WO | WO 2004012627 | A1 | 2/2004 |
| WO | WO 2004/024303 | A1 | 3/2004 |
| WO | WO 2004071349 | A2 | 8/2004 |
| WO | WO 2004103162 | A2 | 12/2004 |
| WO | WO 2005007219 | A2 | 1/2005 |
| WO | WO 2006008429 | A2 | 1/2006 |

* cited by examiner

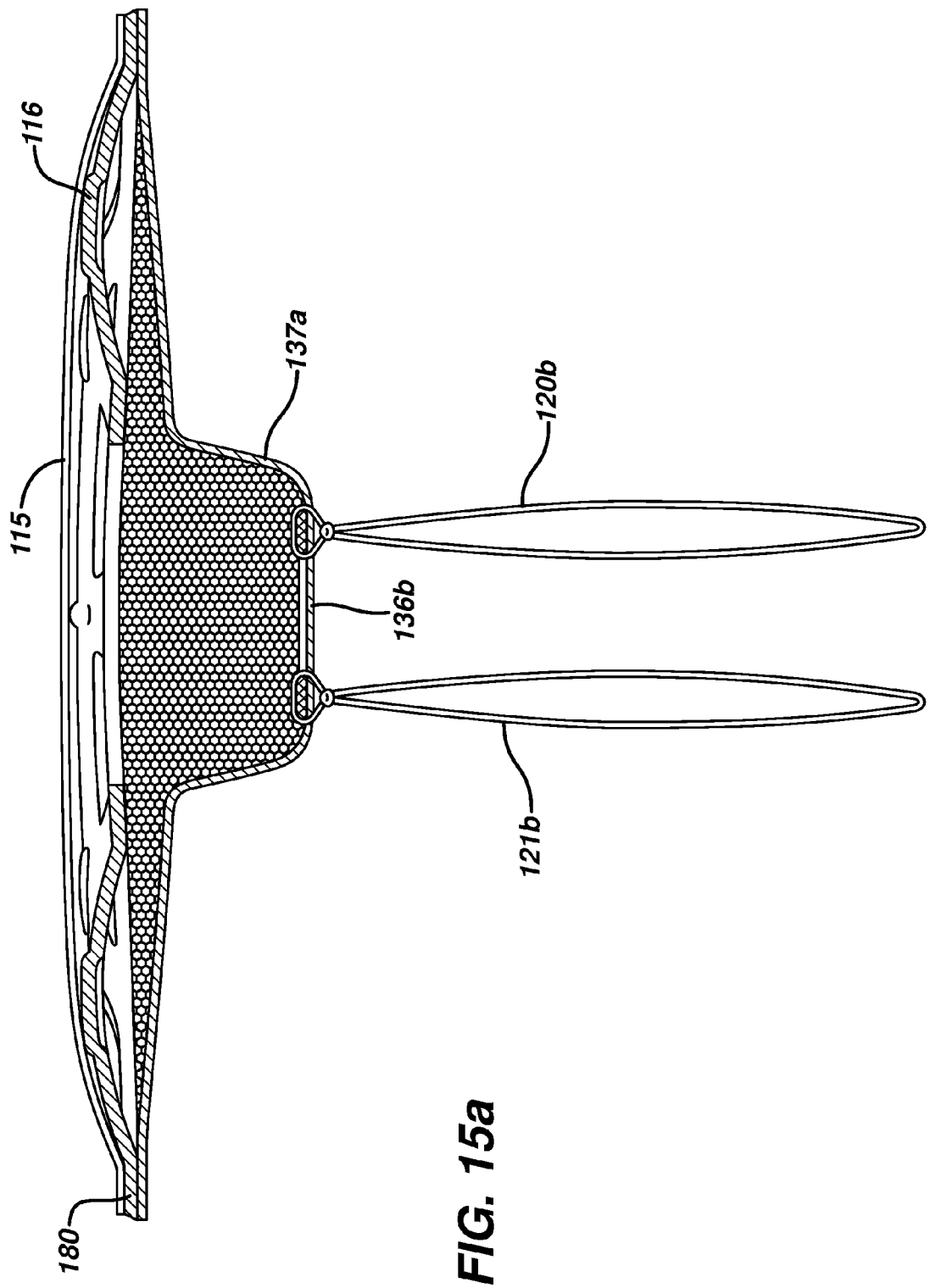

IMPLANTABLE REPAIR DEVICE

BACKGROUND OF THE INVENTION

1. Field of the Invention

The present invention relates generally to implantable prosthesis, and more particularly, to implantable prostheses having particular application for repairing and/or reinforcing an anatomical defect such as a hernia.

2. Background Discussion

Various forms of implantable prostheses have been used for repairing or reinforcing tissue defects, such as soft tissue and muscle wall hernias. For example, it is well known to use an implantable fabric or mesh patch to cover the opening or defect. When an anterior approach is used for the intra-peritoneal ventral hernia repair with a "blind" technique for placing the patch, the patch must be collapsed for passage through the incision and defect, and subsequently released and expanded within the intra-peritoneal space. The patch must then be positioned appropriately, preferably as flat as possible, against the peritoneum. Typically, the side of the patch facing the viscera has tissue barrier characteristics, such as a barrier layer or film. The proper positioning of the patch, however, has proven to be difficult to do through the central access incision in the defect.

More recently, at least one implantable prosthesis is known to include a strap or the like that is secured to a central location of the patch, and extends from the side of the patch that faces the abdominal wall out through the incision to the exterior of the patient's body. This device is described and illustrated in U.S. Pat. No. 7,101,381. The strap provides a means by which to pull on the patch once it is inserted in an effort to secure the patch against the parietal wall, thereby occluding the defect. The strap is either sewn on or otherwise separately secured to the center of the patch, or is constructed in a manner that requires two separate portions to be secured to the patch as shown in FIG. 7 of the publication. Following final placement of the patch, the straps are secured to adjacent fascia or muscle, such as by suturing, with any excess length being trimmed off.

With devices of this type, excess force exerted on the central portion of the patch by the straps can cause the patch to collapse centrally so that the center of the patch begins to pass through the defect, with the radial portion of the patch buckling outwardly (away from the parietal wall) around it. This is extremely undesirable in that buckled or inverted edges expose the unprotected mesh material (portions without a tissue barrier) directly to the internal viscera, increasing the likelihood of undesirable attachments forming between the mesh and the viscera. Further, the securing of the straps to the central portion of the patch may in and of itself compromise the barrier layer. Thus, it is important in any such device to ensure that the patch remains positioned in a uniform plane against the viscera when pulling on the straps to position it.

Although this type of device may incorporate a resilient peripheral "ring" to assist in returning the patch to the desired flat configuration following placement, this ring does not significantly prevent the tendency to buckle as described above. Further, the disclosed ring is comprised of a non-absorbable material, and thus permanently leaves behind a substantial amount of material within the patient. This can be particularly disadvantageous if the ring should ever fracture, which could cause the rough fractured edge(s) to damage surrounding tissue.

Accordingly, it is an object of the present invention to provide improved implantable prostheses for repairing and/or reinforcing soft tissue or muscle wall defects.

SUMMARY OF THE INVENTION

The present invention provides an implantable prosthesis for repairing or reinforcing a tissue or muscle wall defect including a first biocompatible structure having a central portion sized and shaped to cover at least a portion of the tissue or muscle wall defect and having a top side, a bottom side, and first and second extension portions extending laterally outward from opposite sides of the central portion. The prosthesis further includes a reinforcement element positioned adjacent the top side of the patch portion and having a top side, a bottom side, and an outer circumferential edge, and a second biocompatible structure having a top side and a bottom side and at least one opening therethrough, the at least one opening being substantially centrally located. The first and second extension portions of the first structure extend about the outer circumferential edge of the reinforcement element and then inwardly along the top side of the reinforcement element between the reinforcement element and the second structure, to a central portion of the reinforcement element, and then outwardly from the central portion through the at least one opening in the second structure. The first and second structures are further secured to one another at least about a peripheral edge of the prosthesis.

Also provided is an implantable prosthesis for repairing or reinforcing a tissue or muscle wall defect that includes a first composite structure including at least one layer of a non-absorbable material, where the first composite structure has a central portion sized and shaped to cover at least a portion of the tissue or muscle wall defect, and has an outer periphery. The prosthesis further includes a second structure having a reinforced central region and an outer peripheral edge, a reinforcing element positioned between the first and second structures, and having an outer periphery and a stiffness greater than that of the first and second structures, and at least one pulling element coupled to the reinforced central region of the second structure. The second structure is coupled to the first structure substantially only at their respective peripheries.

Finally, also provided is an implantable prosthesis for repairing or reinforcing a tissue or muscle wall defect including a first substantially flat, flexible composite structure including at least one layer of non-absorbable material, the first composite structure having a central portion sized and shaped to cover at least a portion of the tissue or muscle wall defect and having an outer periphery, and a second substantially flat, flexible, structure having an outer periphery substantially similar to the outer periphery of the first structure, and having a reinforced central region. The prosthesis further includes a three-dimensional reinforcing element positioned between the first and second structures and having an outer periphery substantially similar to the outer periphery of the first and second structures, and at least one pulling element coupled to the central region of the second structure. The first composite structure and the second structure are coupled to one another substantially only around their respective outer peripheries.

BRIEF DESCRIPTION OF THE DRAWINGS

FIGS. 15 and 15a are cross-sectional views illustrating alternative embodiments of a prosthesis according to the present invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although the present invention is described in detail as it relates to implantable prostheses for repairing umbilical hernias, it is to be understood that such devices can readily be used for repairing various other soft tissue or muscle wall defects, including but not limited to trocar site punctures, small ventral hernias etc.

Figure 1:
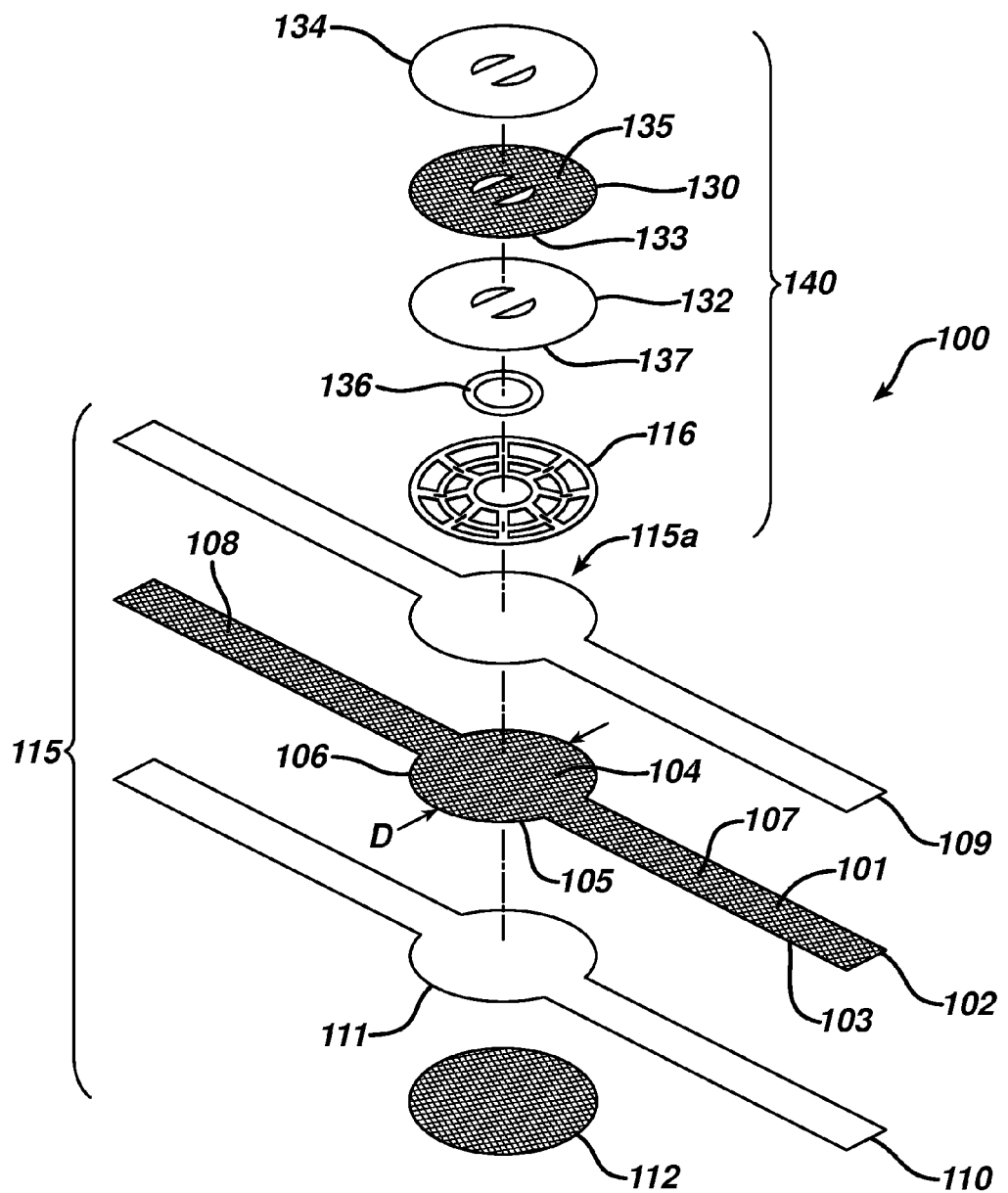
FIG. 1 is an exploded view of the components of a preferred embodiment of a prosthesis according to the present invention.
Figure 1A:
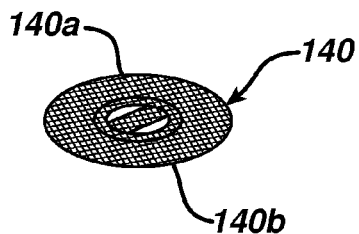
FIG. 1*a* illustrates the prosthesis of FIG. 1 partially assembled.

Referring now to FIGS. 1-8 and 14a-b, a preferred embodiment of a prosthesis of the present invention will now be described in detail. Prosthesis 100 is a composite prosthesis formed from multiple elements as shown in FIG. 1, including a first composite structure 115, a reinforcing element 116 (together the "first reinforced structure"), and a second structure 140. The first structure 115 has a central portion 115a sized and shaped to cover at least a portion of the tissue or muscle wall defect, and preferably first and second extension portions 126, 127 extending laterally outward from opposite sides of the central portion.

The first structure further includes a patch member 102 having a top side 101 and a bottom side 103, and a patch portion 104 corresponding in size and shape to central portion 115a. In the illustrated embodiment, patch portion 104 is substantially circular in overall shape, having a diameter D of approximately 4.3-6.4 cm, which is suitable for repair of a typical umbilical hernia defect. Extending laterally outwardly from opposite sides 105, 106 of the patch portion are first 107 and second 108 extension portions corresponding substantially in size and shape to first and second extension portions 126, 127. The patch member preferably comprises a non-absorbable mesh structure, such as the PROLENE™ Soft Mesh, which is a knitted, non-absorbable polypropylene mesh manufactured by Ethicon, Inc. of Somerville, N.J., although any suitable biocompatible material may be used.

Positioned adjacent the top 101 and bottom 103 sides of the patch portion are first 109 and second 110 film layers respectively, preferably comprised of an absorbable material such as polydioxanone. In a preferred embodiment, the first layer 109 is approximately 0.0002 inches thick and the second layer 110 is approximately 0.0008 inches thick. Positioned adjacent a bottom side 111 of the second film layer 110 is a third layer 112, that also preferably is comprised of an absorbable material. The absorbable material may be oxidized regenerated cellulose (ORC), having a composition such as that manufactured and sold by Ethicon, Inc. under the name INTERCEDE™. The size and shape of the first, second, and third layers are substantially similar to that of the patch portion 104, and may mimic the patch member as a whole as illustrated for the first and second film layers. The components are aligned as shown in FIG. 1, and then secured together in any suitable manner, such as by bonding by heating the assembly to a temperature of approximately 130 degrees Celsius for approximately 30 seconds, to form the first structure 115. When implanted, the third layer 112 provides a bioresorbable layer that physically separates and protects the non-absorbable polypropylene mesh from underlying tissue and organ surfaces during the wound-healing period to minimize tissue attachment to the polypropylene mesh.

While the illustrative embodiment described for structure 115 discloses a composite structure that provides an implant with a barrier surface on one side of the implant while providing a second surface intended to incorporate into the parietal wall, alternate monolithic layers are envisioned which incorporate both functions into one structure. One example of such a monolithic structure is produced by W. L. Gore & Associates, a Delaware Corporation, and sold as GORE DUALMESH®.

Figure 2:
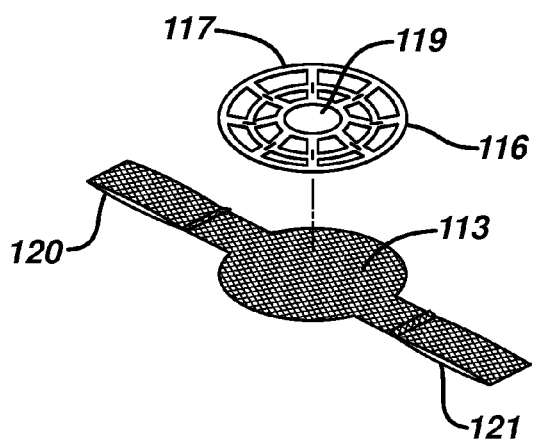
FIGS. 2-5 illustrates the prosthesis of FIG. 1 at various points during assembly.

After forming the first structure 115, the ends of the first and second extension portions 126, 127 respectively are folded over and sewn or otherwise secured in place to form looped elements 120, 121 as best shown in FIG. 2. A reinforcement element 116 (described in detail below), preferably having a substantially similar size and shape as the patch portion 104, is then aligned adjacent a top surface 113 of the first structure 115 as shown in FIG. 2. The first and second extension portions 126, 127 of the first structure are extended around a circumferential edge 117 of the reinforcement element 116 and over the top side 118 to a central portion 119 of the reinforcing element as shown in FIG. 3.

Referring back to FIG. 1, the preferred embodiment of the prosthesis also includes a second structure 140 having an outer periphery 143 and a central region 143a. The second structure further includes a second mesh layer 130, third and fourth film layers 132, 134 positioned adjacent top bottom and top 133, 135 sides thereof, and a separate stiffening element 136 in the central region, preferably a film ring, having an outer diameter less than that of film layers 132, 134 and positioned adjacent a bottom side 137 of the third 132 film layer. The second mesh layer 130 is preferably made of a synthetic, absorbable material, such as VICRYL™ Mesh, which is prepared from polyglactin 910 and also manufactured and sold by Ethicon, Inc. of Somerville, N.J. The third and fourth film layers and film ring are preferably comprised of polydioxanone. The layers are aligned as illustrated and bonded together to form a second structure 140 having a top side 140a and a bottom side 140b. Alternatively, this composite structure may be replaced be a monolithic layer that is formed of varying stiffness regions with the central portion having significantly greater stiffness than the regions near the perimeter of the layer.

Figure 3:
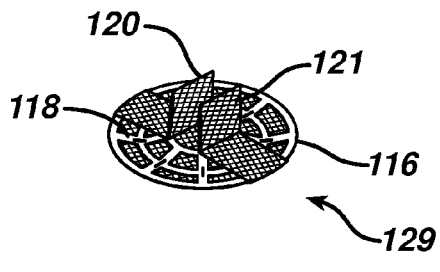
Figure 4:
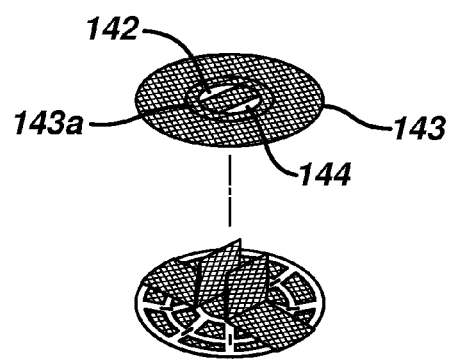
Figure 5:
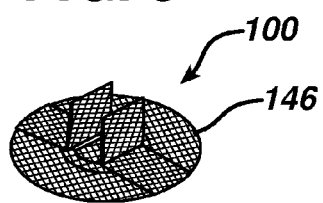
Figure 6:
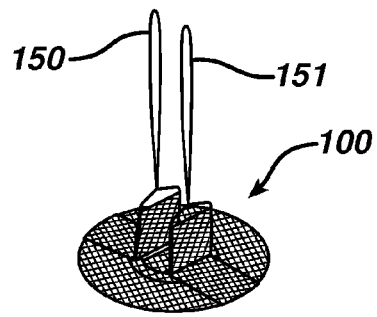
FIG. 6 illustrates the prosthesis of FIG. 1 fully assembled.

The first reinforced structure 129 shown in FIG. 3 and the second structure 140 are then aligned as shown in FIG. 4 so that the first and second loops 120, 121 extend through first and second openings 142, 144 through the second structure 142 as shown in FIG. 5, and then bonded (i.e., via ultrasonic welding), fused, sewn, or otherwise joined together substantially only around their respective outer peripheries with the exception of extension portions 126, 127 as described below. Finally, additional grasping elements 150, 151, such as an ETHIBOND™ polyester suture or the like (also manufactured by Ethicon, Inc.), may be inserted through the first and second loops 120, 121 as shown in FIG. 6.

Figure 14A:
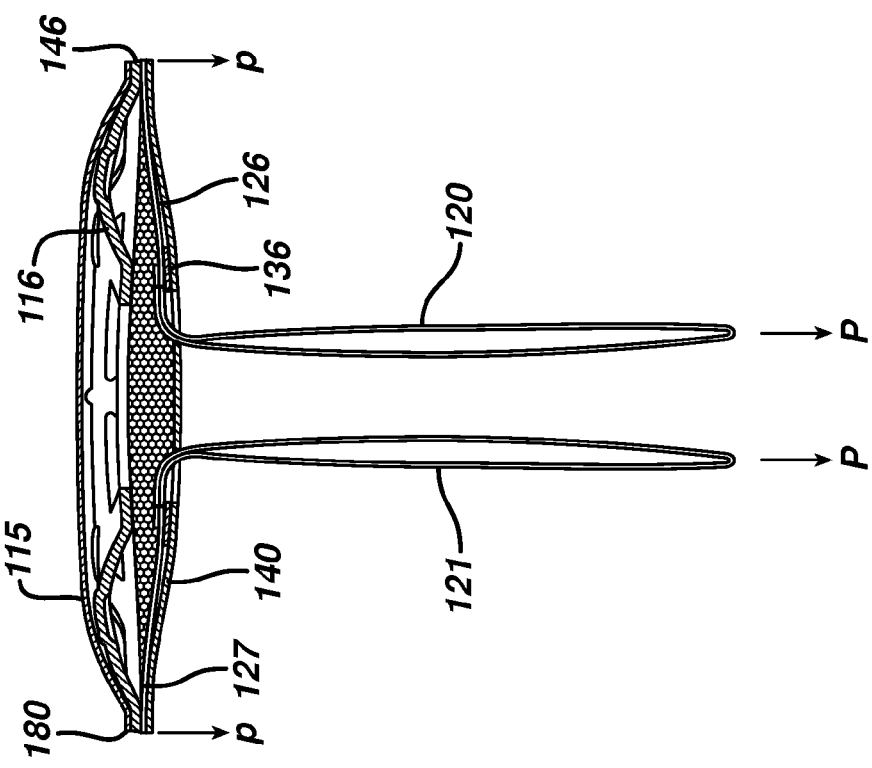
FIGS. 14a and 14b are a cross-sectional views of the embodiment of FIG. 5.
Figure 14B:
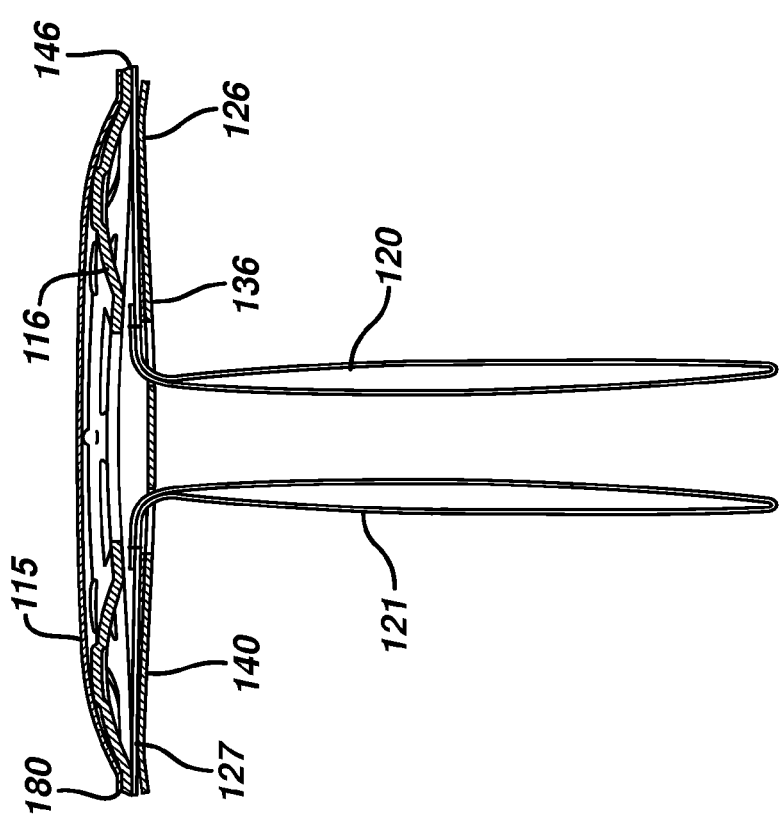

As indicated, film ring 136 is bonded to the second structure 140, but is not bonded to the first reinforced structure. Further, the first and second extension portions 126, 127 are coupled to the film ring 136 of the second structure and are not otherwise secured to the first reinforced structure other than around the peripheral edge. This configuration is advantageous in that it enables a centralized force exerted on the first and second loops 120, 121 to be distributed to the film ring 136, and thus distributed substantially uniformly through the second structure 140 and ultimately to the outer periphery 146 of the prosthesis, which is reinforced by the outer circumferential ring 180 of the reinforcement element. This distribution of forces is illustrated in the cross-sectional view of FIG. 14b, where P denotes the pulling force exerted on the loops 120, 121 and p denotes the resulting forces experienced by the prosthesis (as opposed to FIG. 14a illustrating the device with no pulling forces being exerted on it). This substantially uniform distribution of centralized forces to the outer periphery of the implant provides significant improvements over known devices in the ability to avoid point stresses and potential damage to the implant at the attachment point(s) of the straps, and to implant and correctly place the prosthesis.

Figure 15:
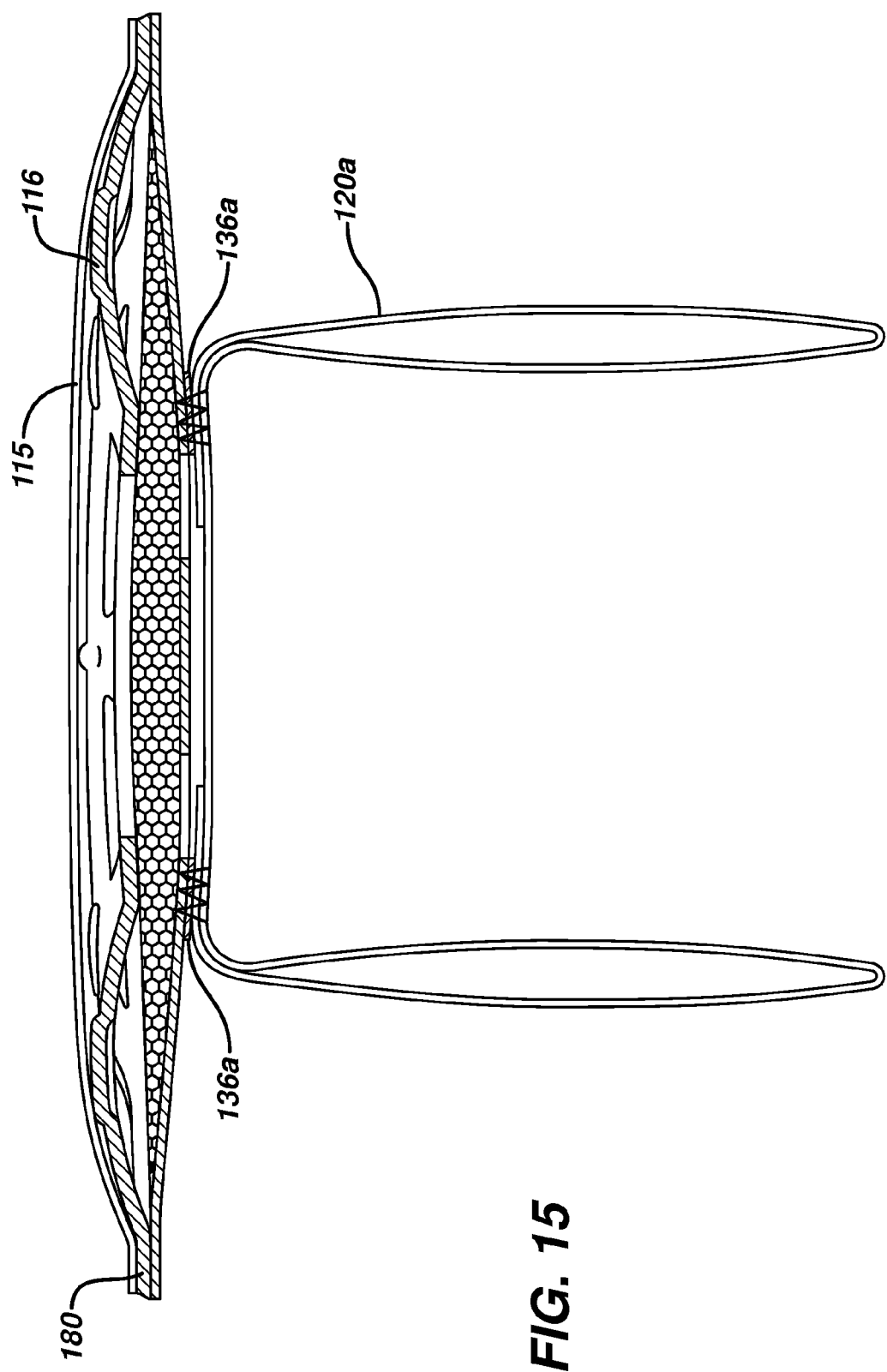

The effective redistribution of forces as described above is achieved with the described and illustrated preferred embodiment, but can also be achieved in various other alternative embodiments so long as central straps or other pulling elements are secured to a centrally reinforced second structure that is coupled to the first reinforced structure substantially only about its peripheral edge. For example, an alternate embodiment could include a single 120a or separate straps that are coupled or secured by any suitable means to a ring element 136a of a second structure 140a as shown in FIG. 15, or may utilize one or more pulling elements 120b, 121b or grasping means attached to a substantially solid central element 136b as shown in FIG. 15a. Both embodiments enable the distribution of loading during tensioning, however the embodiment illustrated in FIG. 15a provides a three dimensional central portion 137a capable of at least partially filling the defect in the fascial plane.

Figure 7:
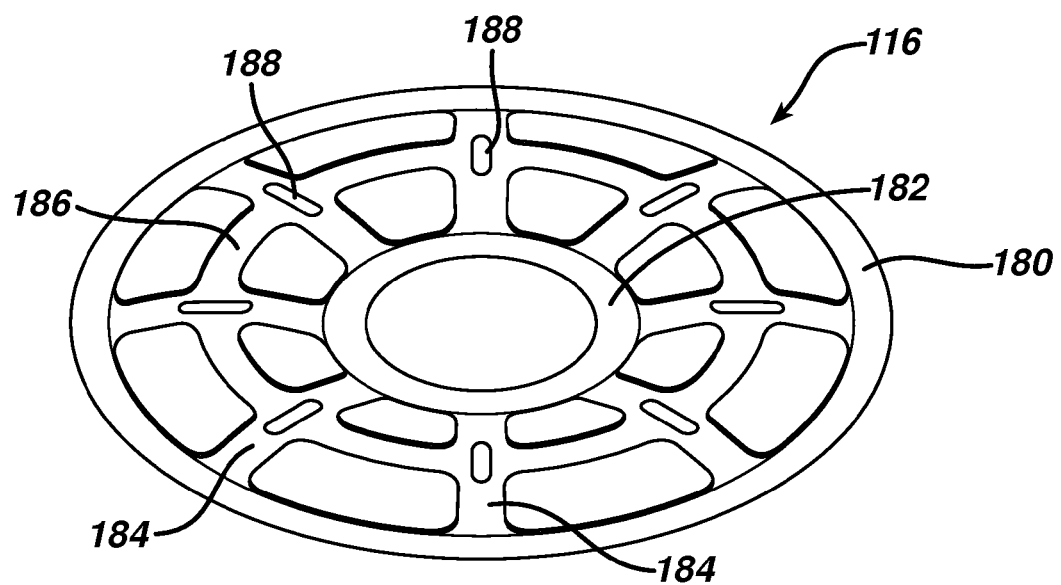
FIGS. 7-8 are perspective and side views of the reinforcement element of the prosthesis of FIG. 1.
Figure 8:

Referring now to FIGS. 7 and 8, the reinforcing element 116 serves to reinforce the implant, and maintain its proper substantially flat orientation covering the defect within the patient's body. The reinforcing element must be flexible enough to allow it to be collapsed for passage through the incision and defect, but resilient enough to resume the substantially flat configuration once properly placed. The element should control, in part or in whole, the direction of strain when subjected to a radial compressive force. Additionally, the reinforcing element must not inhibit tissue incorporation into the tissue support layer and should provide means for the healing tissue to pass through to the tissue support layer. The resilient element described and illustrated herein has been found particularly suitable for these purposes, and its preferred three-dimensional configuration greatly improves resistance to collapsing or buckling of the implant after placement.

The three dimensional form provides the additional benefit of controlling the direction of strain of the implant during placement. During installation and following insertion of the device through the defect, the first and second loops 120, 121 are pulled on by the surgeon to ensure a proper and tight fit of the implant relative to the defect. During this application of tension to the straps, the force from the user is distributed from the center of the device uniformly to the perimeter of the reinforcing layer thereby creating a radial compressive load in the reinforcing layer. As this compressive loading increases on the reinforcing layer, the strain in the reinforcing layer is directed towards the center of the device and, in the preferred direction, away from the parietal wall. This controlled direction of strain results in the perimeter of the device conforming tightly to the parietal wall due to the increased strain in the third dimension of the form or "cupping" of the reinforcing layer. This improved compliance of the perimeter of the device prevents the user from collapsing the device in a direction that would cause exposure of the side of the device to the viscera. While the specific embodiment incorporates a semitoroidal shape, it should be noted that any symmetrical three dimensional form, such as a spherical shape, would provide the same functional benefit during installation. As shown in the side view of FIG. 8, the reinforcing element preferably has a three-dimensional ("three-dimensional" meaning having a third dimension other than simple thickness of a planar structure), somewhat toroidal shape, with an outer circumferential ring 180 of the element lying substantially in a first horizontal plane and an inner circumferential ring 182 lying substantially in a second horizontal plane. Spoke like elements 184 extend therebetween, and in the illustrated embodiment, an intermediate circumferential ring 186 is positioned between the outer circumferential ring 180 and the inner circumferential ring 182. The reinforcing element is preferably made of an absorbable material, such as polydioxanone, with a thickness of approximately 0.015 inch which renders its stiffness greater than that of the first or second structures 115, 140. In a preferred embodiment, it may further include one or more rib-like elements 188 extending longitudinally along portions of the spoke-like elements 184. The rib elements further reinforce and provide stability to the implant and prevent permanent inversion of the formed shape from transient compression perpendicular to the plane of the center portion of the three dimensional reinforcing layer. The three-dimensional geometry and configuration of the reinforcing element has proven to be superior over two-dimensional geometries in achieving an optimum combination of flexibility, rigidity, resistance to buckling, and controlling the direction of strain for the above-described application.

Figure 9:
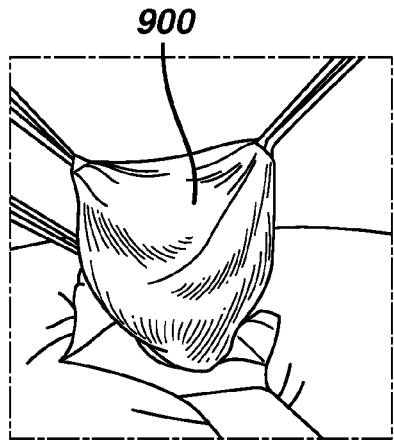
FIGS. 9-13 illustrate various steps of a procedure for implanting a prosthesis according to the present invention.
Figure 10:
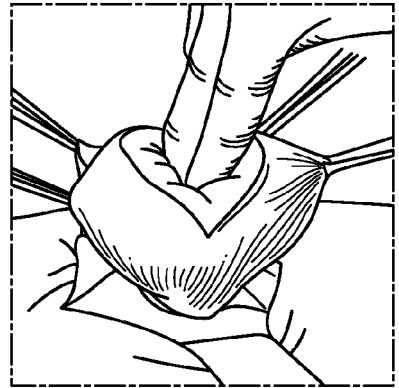
Figure 11:
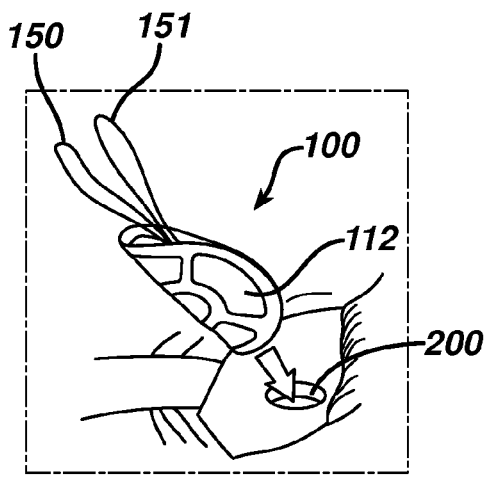
Figure 12:
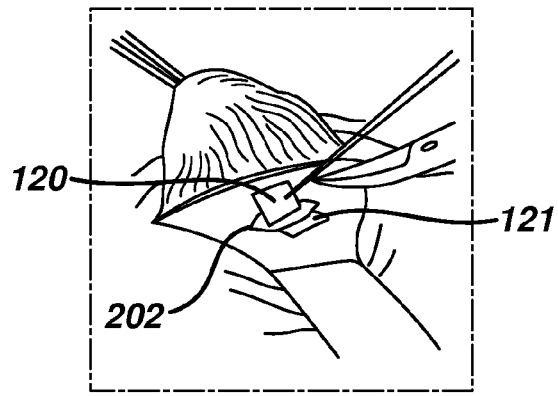
Figure 13:
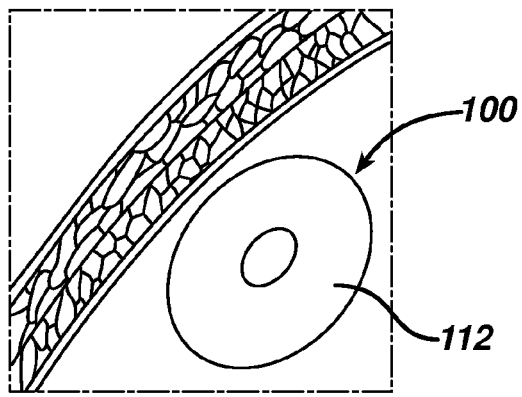

FIGS. 9-13 illustrate various steps of a method for implanting a prosthesis according to the present invention. The skin and tissue in the area of the defect is dissected to provide access to the surgical site. Preferably, the hernia sac is exposed as illustrated in FIG. 9, with the sac divided and contents inverted as shown in FIG. 10. The patch 100 is folded over with the side containing the straps on the interior of the fold, and the exposed ORC fabric layer 112 on the exterior of the fold as shown in FIG. 11. The patch 100 is then delivered into the surgical site through the incision 200. This may be done in any suitable manner, including with or without the use of a cannula or trocar to facilitate its passage. When the patch is fully within the intra-peritoneal space, the patch is released from its folded configuration so that it resiliently resumes its original, substantially flat configuration. Proper positioning against the internal viscera in the substantially flat configuration (with the ORC fabric layer 112 facing the internal viscera) is further facilitated by pulling slightly on the grasping elements 150, 151. Following suitable placement, loops 120, 121 are secured to the anterior fascia as shown in FIG. 12, leaving the implanted patch as shown in FIG. 13.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. An implantable prosthesis for repairing or reinforcing a tissue or muscle wall defect, comprising:
   a first biocompatible structure having a central portion sized and shaped to cover at least a portion of the tissue or muscle wall defect and having a top side, a bottom side, and first and second extension portions extending laterally outward from opposite sides of the central portion;

a reinforcement element positioned adjacent the top side of the first structure and having a top side, a bottom side, and an outer circumferential edge the reinforcement element having a plurality of openings therethrough, wherein the reinforcement element is at least partially flexible and collapsible; and a second biocompatible structure having a top side and a bottom side and at least one opening therethrough, the at least one opening being substantially centrally located;

wherein the first and second extension portions of the first structure extend about the outer circumferential edge of the reinforcement element and then inwardly along the top side of the reinforcement element between the reinforcement element and the second structure, to a central portion of the reinforcement element, and then outwardly from the central portion through the at least one opening in the second structure and beyond the top side of the second structure, the first and second structures being secured to one another at least about a peripheral edge of the prosthesis.

2. The prosthesis according to claim 1, wherein the reinforcement element has a stiffness greater than a stiffness of the first and second structures.

3. The prosthesis according to claim 1, wherein the reinforcement element further comprises an outer circumferential ring and an inner circumferential ring and a plurality of spoke elements extending therebetween.

4. The prosthesis according to claim 1, wherein the reinforcement element has a three-dimensional shape.

5. The prosthesis according to claim 1, wherein distal ends of the first and second extension portions are folded over to form first and second looped elements, and further comprising first and second grasping members secured to the first and second looped elements respectively.

6. The prosthesis according to claim 1, wherein the first structure further comprises:
 a patch member comprised of a non-absorbable mesh; and
 first and second absorbable film layers positioned adjacent top and bottom sides of the patch member respectively and secured thereto.

7. The prosthesis according to claim 6, wherein the patch member is comprised of polypropylene and the first and second film layers are comprised of polydioxanone.

8. The prosthesis according to claim 6, wherein the first structure further comprises a third layer of an absorbable material positioned adjacent to a bottom side of the second film layer and secured thereto.

9. The prosthesis according to claim 1, wherein the second structure further comprises a ring element having an outer diameter less than an outer diameter of the second structure, and wherein the first and second extension portions of the first structure are coupled to the ring element.

10. The prosthesis according to claim 9, wherein the second structure further comprises a mesh layer, and third and fourth film layers positioned adjacent top and bottom sides respectively of the mesh layer and secured thereto, and wherein the mesh layer and third and fourth film layers of the second structure are comprised of an absorbable material.

11. An implantable prosthesis for repairing or reinforcing a tissue or muscle wall defect, comprising:
 a first biocompatible structure having a central portion sized and shaped to cover at least a portion of the tissue or muscle wall defect and having a top side, a bottom side, and first and second extension portions extending laterally outward from opposite sides of the central portion;
 a reinforcement element positioned adjacent the top side of the first structure and having a top side, a bottom side, and an outer circumferential edge, wherein the reinforcement element further comprises rings and a plurality of spoke elements extending therebetween; and,
 a second biocompatible structure having a top side and a bottom side and at least one opening therethrough, the at least one opening being substantially centrally located;
 wherein the first and second extension portions of the first structure extend about the outer circumferential edge of the reinforcement element and then inwardly along the top side of the reinforcement element between the reinforcement element and the second structure, to a central portion of the reinforcement element, and then outwardly from the central portion through the at least one opening in the second structure, the first and second structures being secured to one another at least about a peripheral edge of the prosthesis.

12. The prosthesis according to claim 11, wherein the reinforcement element has a stiffness greater than a stiffness of the first and second structures.

13. The prosthesis according to claim 11, wherein the reinforcement element has a three-dimensional shape.

14. The prosthesis according to claim 11, wherein distal ends of the first and second extension portions are folded over to form first and second looped elements, and further comprising first and second grasping members secured to the first and second looped elements respectively.

15. The prosthesis according to claim 11, wherein the first structure further comprises:
 a patch member comprised of a non-absorbable mesh; and
 first and second absorbable film layers positioned adjacent top and bottom sides of the patch member respectively and secured thereto.

16. The prosthesis according to claim 15, wherein the patch member is comprised of polypropylene and the first and second film layers are comprised of polydioxanone.

17. The prosthesis according to claim 15, wherein the first structure further comprises a third layer of an absorbable material positioned adjacent to a bottom side of the second film layer and secured thereto.

18. The prosthesis according to claim 11, wherein the second structure further comprises a ring element having an outer diameter less than an outer diameter of the second structure, and wherein the first and second extension portions of the first structure are coupled to the ring element.

19. The prosthesis according to claim 18, wherein the second structure further comprises a mesh layer, and third and fourth film layers positioned adjacent top and bottom sides respectively of the mesh layer and secured thereto, and wherein the mesh layer and third and fourth film layers of the second structure are comprised of an absorbable material.

* * * * *